United States Patent
Moriyoshi

[11] Patent Number: 5,394,753
[45] Date of Patent: Mar. 7, 1995

[54] MATERIAL TESTING DEVICE AND TESTING METHOD THEREBY

[76] Inventor: Akihiro Moriyoshi, 9-10, Nijo 1-chome, Kiyota, Toyohira-ku, Sapporo-shi, Hokkaido, Japan

[21] Appl. No.: 963,982

[22] Filed: Oct. 20, 1992

[30] Foreign Application Priority Data

Oct. 30, 1991 [JP] Japan .................. 3-314006

[51] Int. Cl.⁶ .................................................. G01N 3/08
[52] U.S. Cl. .................................................. 73/818
[58] Field of Search ............................ 73/818–823, 73/825–828, 830–835, 837, 849, 851, 853, 854

[56] References Cited

U.S. PATENT DOCUMENTS

| | | | |
|---|---|---|---|
| 2,699,060 | 1/1955 | Safford | 73/823 |
| 2,732,708 | 1/1956 | Linhorst | 73/822 |
| 4,266,424 | 5/1981 | Muenstedt | 73/826 |
| 4,313,289 | 2/1982 | Birdsong, Jr. | 73/818 |
| 4,475,404 | 10/1984 | Rutledge, Jr. et al. | 73/827 |
| 5,105,626 | 4/1992 | Gonczy et al. | 62/511 |

FOREIGN PATENT DOCUMENTS

| | | | |
|---|---|---|---|
| 1559519 | 3/1969 | France | 73/818 |
| 63-145167 | 9/1988 | Japan . | |
| 64-11146 | 2/1989 | Japan . | |
| 2207 | 6/1990 | Japan . | |
| 380155 | 9/1932 | United Kingdom | 73/821 |

Primary Examiner—Robert Raevis
Attorney, Agent, or Firm—Flynn, Thiel, Boutell & Tanis

[57] ABSTRACT

A testing device which makes structure of equipment simple, achieves dwarfing and lightening and can improve precision of measurement of tested material. And method to implement test of strength of fracture, fracture temperature, strain at fracture, viscosity and stress relaxation (relaxation modulus) and so on of test piece handily.

6 Claims, 5 Drawing Sheets

MATERIAL TESTING DEVICE AND TESTING METHOD THEREBY

BACKGROUND OF THE INVENTION

1. Field of the Invention

This invention relates to a material testing device, especially, with a testing device and a testing method to measure brittle point, fracture strength, strain of fracture, viscosity and stress relaxation (relaxation modulus of elasticity) and so on in comparatively low strength's materials like asphalt, wax, resin and the paint and the food of chocolate and so on.

2. Description of the Related Art

As the method of measuring brittle point in the comparatively low strength's material like asphalt, wax, resin and the paint and the food of chocolate and so on, Fraass brittle point test method (JIS K2207 "PETROLEUM ASPHALT" 5.15 page; the conventional example 1) is known from the past.

In the above-mentioned conventional example 1, it is necessary to confirm an occurrence of crack in the material to be tested with the eyes through a test tube made from the glass. But, when the test tube becomes dim with cooling air, the such confirmation is difficult. Also, there is a problem that it is difficult to get high precision measurement results because it isn't possible to control the rate of cooling correctly.

As the method to improve these problems, the following methods are proposed; Fraass brittle point test method (Japanese Patent Application Publication Sho 64-11146; the conventional example 2) which catches a noise which accompanies the occurrence of crack in the tested material and detects temperature at this time; and another Fraass brittle point test method (Japanese Utility-model Application Laid-open Sho 63-145167; the conventional example 3) which makes the tested material curve repeatedly in liquid, and measures temperature of the liquid when crack occurs in the tested material.

SUMMARY OF THE INVENTION

The material testing device of the present invention has characteristics of having the first and the second members which are relatively displaced, the test piece attachment provided between one sides of the above-mentioned first and the second members which can bend the test piece by the relative displacement of the first and the second members, the drive device to displace the above-mentioned first and second members by being positioned between the other sides of the first and the second members and the detection device which is positioned between the above-mentioned drive device and the first member or between the drive device and the second member capable of detecting the load thereof.

Also, it is desirable that a vessel which contains the above-mentioned test piece is provided with a stationary device for the first or the second members. For example, an elastic material such as sponge or rubber should be installed in the periphery of the first or second member and a hole to insert the above mentioned elastic material on the lid should be made.

A testing method of this invention has characteristics of installing the test piece on the test piece attachment of the device and bending the test piece by the relative displacement of the first and the second members.

Besides, it is desirable that the above-mentioned testing method be used for a stress relaxation test to estimate the deformation of materials based on a brittle point, fracture strength, strain at fracture of the material, or a relation between the deformed quantity and the distortion.

Incidentally, an outside cylinder and an inside cylinder each of which are arranged coaxially can be adopted as the first and second members.

Also, as the test piece attachment, an end of the second member should be projected from the end of the first member and a pair of clips facing each other at each end should be provided.

Moreover, as the drive device, the nut member screwing the screw member on the other end of the first member should be fixed and the other end of the second member should be formed in the shape of a blade which is projecting from the above-mentioned first member in the axial direction and the structure urging the other end of the second member in the axial direction by the movement of the screw member.

As a means of detection of the load which acts on the test piece, between the above-mentioned drive device and the other end of the first member or between the drive device and the other end of the second member, the load cell which can detect the load change should be positioned.

Also, the distortion or the stress of the test piece can be found by the distortion of the center of the test piece measured in advance and the calibration curve of the deformation quantity or the relation between the load and distortion speed after attaching a gage to the test piece.

In the present invention, the drive device is positioned between the first and the second members. Therefore, it is unnecessary to fix each separately to the vessel which contains the test piece.

Also, because between the drive device and the other end of the first member or between the drive device and the other end of the second member the detection device is positioned, the load change in the bending test piece can be directly detected as the load change in the detection device, so that the high-precision measurement result is acquired.

Moreover, because in the first or second member, easily detachable stationary means is used to the container which contains the test piece, complicated operation is not needed to replace the test piece.

Therefore, it is possible to simplify the whole structure and to improve the measurement precision, whereby the above-mentioned purpose is achieved.

DETAILED DESCRIPTION OF THE PREFERRED EMBODIMENT(S)

Hereinafter, a preferable embodiment of the invention will be described in detail with reference to the attached drawings.

Figure 1:
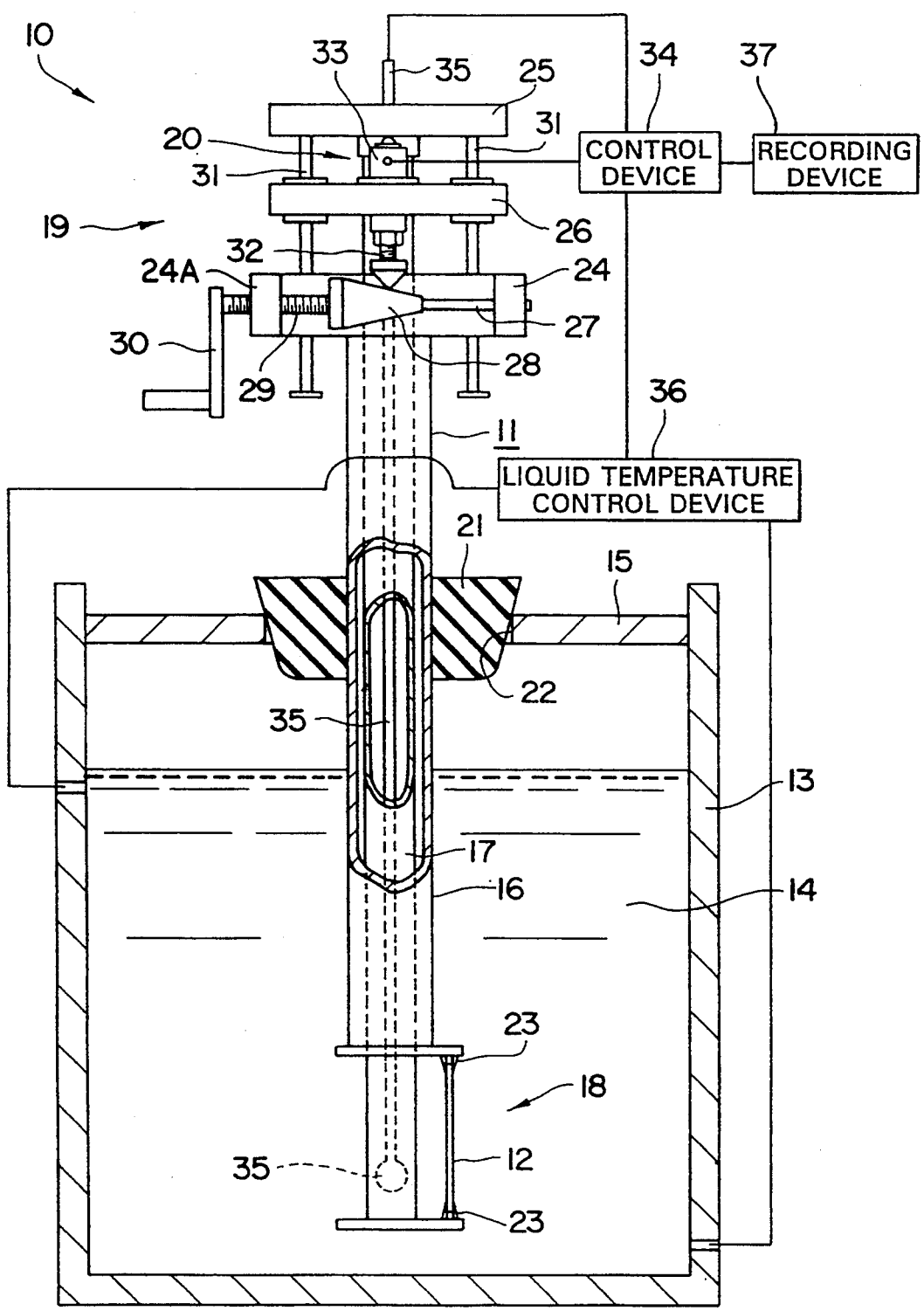
FIG. 1 is the sectional front view which shows the preferable embodiment according to the present invention.
Figure 2:
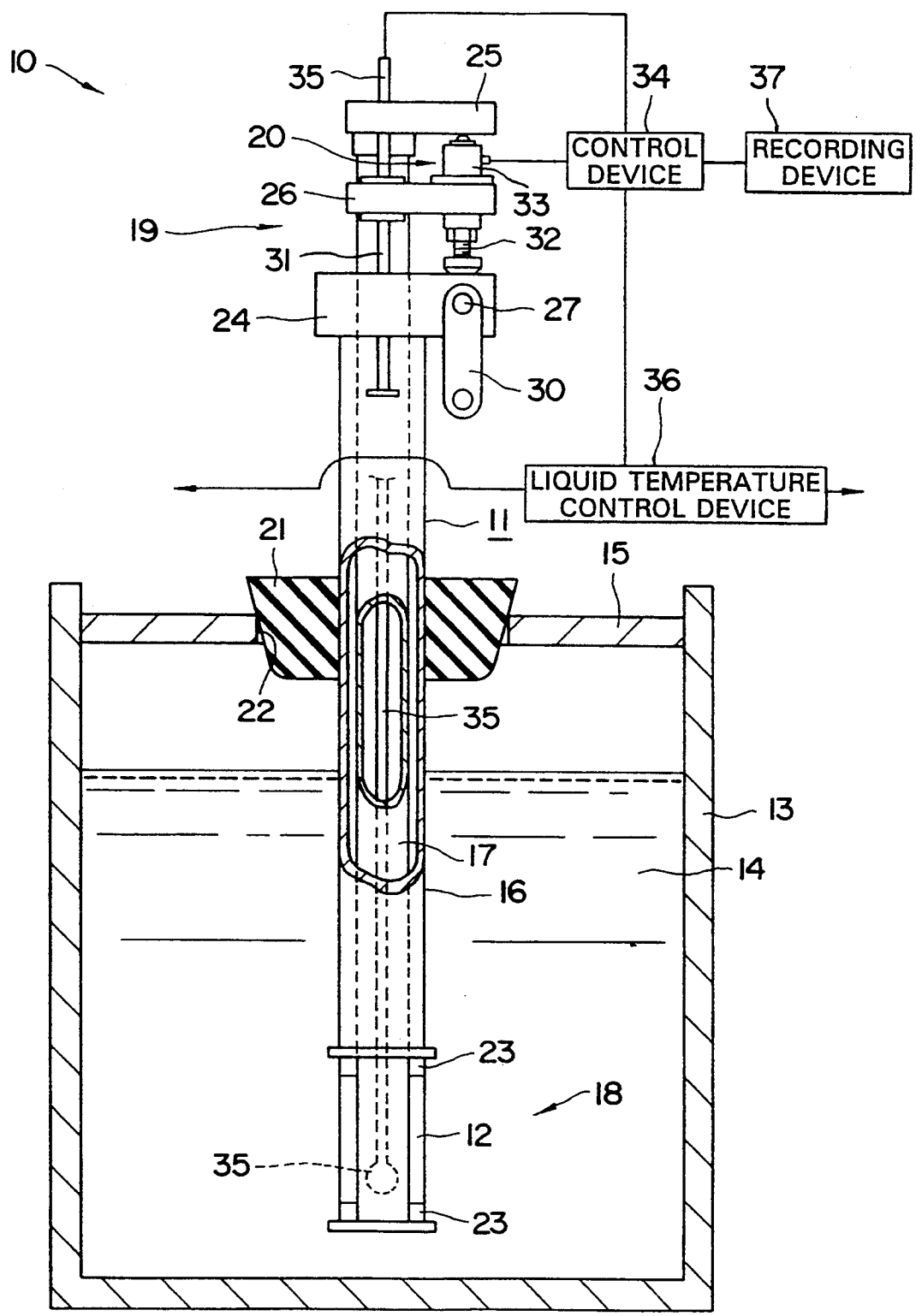
FIG. 2 is the sectional side-view diagram which shows the above mentioned embodiment.

The preferable embodiment based on the present invention is shown in FIGS. 1 and 2. A testing device 10 for the tested material shown in the drawings is for strength testing of a concerned test piece 12 by steps of soaking the test piece 12 attached to a body 11 of the device into a liquid 14 which is stored up in a liquid vessel 13 and curving repeatedly the thus-soaked test piece 12 with the going-up and down of the liquid temperature of liquid 14.

The test piece 12 is in the state that the tested material is applied to one side of a base plate with the fixed dimension which has elasticity like the metal, plastic and so on.

The body 11 of the device includes an outside pipe 16 as the first member which is installed in the condition which stands to a lid 15 of the liquid vessel 13 and an inside pipe 17 as the second member which moves relatively along an axial direction in the inside of the outside pipe 16.

Either of the outside pipe 16 and the inside pipe 17 are pipes double arranged coaxially.

The outside pipe 16 is equipped with a stationary member 21 at the approximately middle part of the axial direction. The stationary member 21 is formed to taper off to the end thereof with the material which has elasticity, e.g. sponge, rubber and so on. Such stationary member is put into a fixation hole 22 which was opened to the lid 15 and the outside pipe 16 is fixed standing so that attachment and removal to the lid 15 can be done.

The inside pipe 17 projects by fixed dimension respectively from both bottom and upper end of the outside pipe 16.

The outside pipe 16 and inside pipe 17 are equipped with a test piece attachment 18 at the bottom portions thereof and a drive means 19 at the upper end portions thereof. Also, a detection device 20 intervenes between the drive device 19 and the inside pipe 17.

The test piece attachment 18 has one pair of clips 23 which were provided at each bottom portion of the pipes 16 and 17 in a state that they confront along the axial direction.

The clips 23 can pick and keep the test piece 12 at both edges on top and bottom thereof, whereby the test piece 12 is compressed into the lengthwise direction and curves when the outside pipe 16 and the inside pipe 17 move relatively.

The drive device 19 is structured with a support member 24 which is set up on the upper end of the outside pipe 16 and a pressure plate 25 which is set up on the upper end of the inside pipe 17 and also includes a sliding member 26 which is arranged between the support member 24 and the pressure plate 25.

The support member 24 is C-shaped and planar and has a revolving shaft 27 supported on and extending between the two opposite sides of the member 24 so that it can rotate. The revolving shaft 27 has a tapered part 28 almost in the axial center and has a male threaded portion 29 extending from the tapered part 28 to one end thereof. Also, a handle 30 is attached on the proximal edge, i.e. at the left end of the shaft 27 as shown in the drawing. One side 24A of the support member 24 has an internally threaded hole threadedly receiving therein the male threaded portion. When the handle 30 is rotated, the revolving shaft 27 moves forward or backward by means of the male threaded portion 29.

The pressure plate 25 has one pair of guide members 31 extending from the underside thereof. The guide members 31 each extend through a part of the support member so as to slide with respect to the support member 24 freely at their lower portions.

The sliding member 26 is pierced with the guide member 31 extending through the piercing so that it can slide in the axial direction along the outside pipe 16 and the inside pipe 17. The member 26 has an adjustment bolt 32 being almost cone-shaped and extending downwardly to touch the tapered part 28 of the support member 24. Accordingly, the sliding member 26 goes up and down reciprocally by the movement of tapered part 28 caused by the rotation of the handle 30. An altering of its height position by adjusting the adjust bolt 32.

The detection device 20 has a structure which includes a load cell 33 arranged on a surface of sliding member 26 of which an upper end thereof abuts the pressure plate 25, the load cell 33 outputting a compressive load signal between the outside pipe 16 and the inside pipe 17 and the thus-output signal is transmitted to a control device 34 electrically connected.

Figure 3:
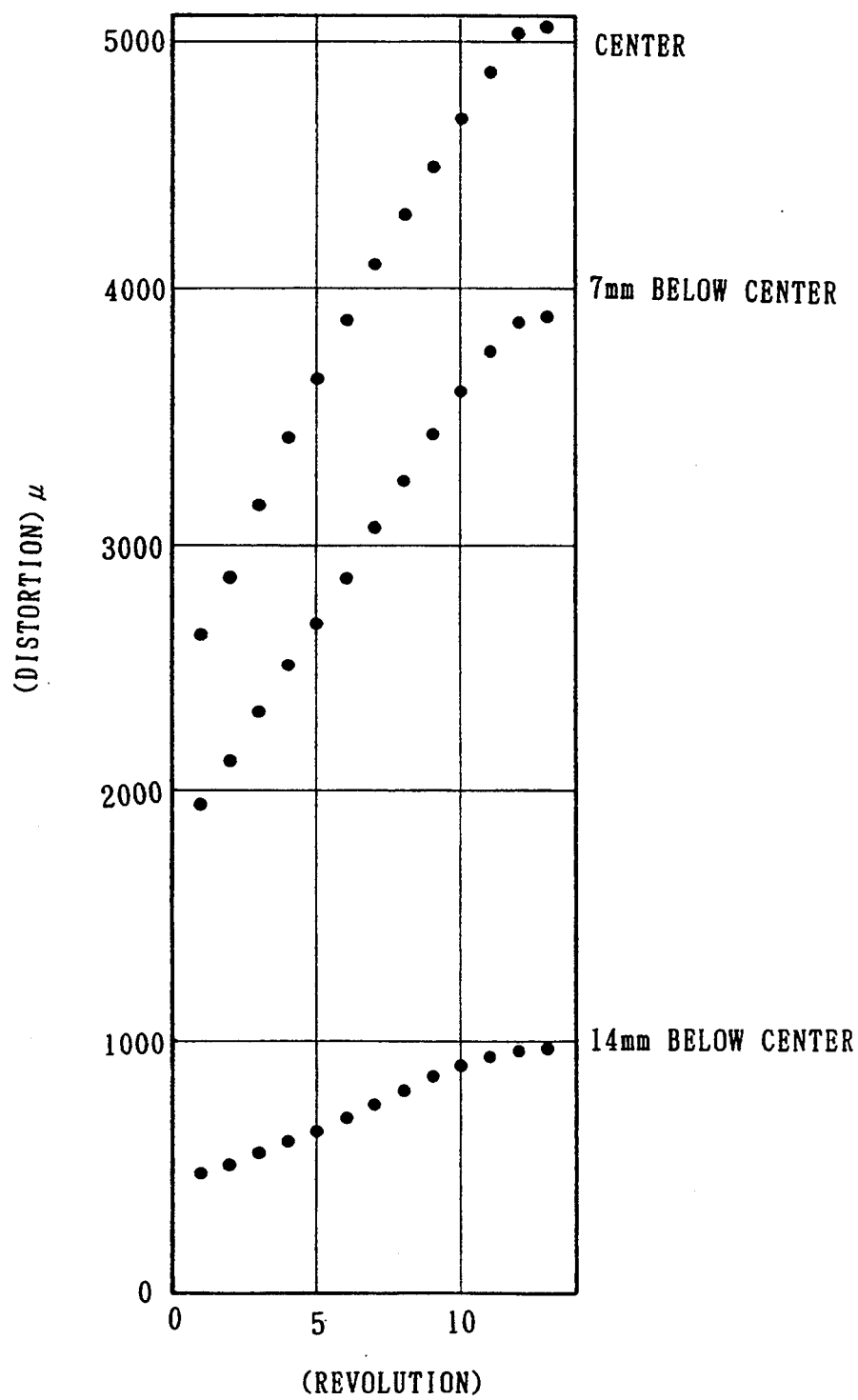
FIG. 3 is the graph which shows a relation between the distortion of the test piece and the revolution of the handle.

As shown in FIG. 3, the distortion of the test piece 12 is found from a relation between the revolution of handle 30 and the distortion at the center of the test piece which has been estimated beforehand. In the drawing, the revolution 0 (zero) shows the state before installing the test piece 12 to the clips 23 and the revolution 1 shows the state after installing the test piece 12 to the clip 23.

The control device 34 is not only connected with the above-mentioned load cell 33, but also a liquid temperature gage 35 to detect the temperature of liquid near the test piece 12 in the liquid vessel 13, a liquid temperature control device 36 which controls the temperature of liquid 14, and a recording device 37 which records inputted data and so on appropriately.

The liquid temperature gage 35 has a length which extends to the inside pipe 17 from the top to the bottom thereof, outputs the signal, to the outside from its top portion, which shows the liquid temperature detected at its lower exposed part.

The liquid temperature control device 36 is provided to make the temperature of the liquid up and down and then adjust it to a constant temperature by rotating the liquid 14 appropriately according to signals from the control means 34.

The procedure of the test for materials using the testing device, which was structured as above mentioned, will be explained hereafter.

First, the test piece 12 is put to the test piece attachment 18 of the body of equipment 11, one end of the body of equipment 11 where the test piece attachment 18 is provided is inserted into the fixation hole 22, and then, by putting the stationary member 21 in the fixation hole 22 so that the test piece 12 is soaked in the liquid 14, whereby the body of the concerned equipment 11 can stand on the lid 15.

When rotating the handle 30 and then-making the pressure plate 25 go up and down through the sliding, member 26, whereby the test piece 12 can reciprocally by curve or bend caused by the relative movement of the outside pipe 16 and the inside pipe 17. Concretely, when the handle 30 is revolved in clockwise direction, the test piece 12 bends. While the handle 30 is revolved in the reverse direction, the curve or bending of test piece 12 is released.

A relation between the revolution of the handle 30 and the deformation of test piece 12 is shown in FIG. 3 by fitting a gage on the test piece 12. In the drawing, the horizontal axis shows the revolution of the handle 30 and the vertical axis shows the distortion of the test piece 12, wherein the maximum distortion of the test piece 12 at its center can be found.

When controlling the temperature of liquid 14 up or down depending upon a test condition with the liquid temperature control means 36 based on instructions from the control device 34 while alternately repeating curve or bending and recovery of the test piece 12, whereby when the liquid temperature reaches a predetermined-level which corresponds to the brittle point of the tested material, the pressure of load cell 33 acted upon by the pressure plate 25 declines rapidly.

This decline of the pressure can be detected by the control device 34. The control device 34 further has functions to output, in recording device 37, signals from the liquid temperature gage 35 and liquid temperature data from the liquid temperature control device and to record a measurement result in a record form. Accordingly, the brittle point of test piece can be detected.

Incidentally, a distortion at when a tested material is destroyed is synthetically found from the revolution of handle 30 and the curve shown in FIG. 3. Moreover, it may be possible to implement a stress relaxation test if a correct vertical displacement of the test piece and a correct measurement of stress are done.

Many test pieces can be examined by pulling the stationary member 21 out of the fixation hole 22, sequentially exchanging the test piece 12 attached to the test piece attachment 18.

According to the above-mentioned embodiment, because the drive device 19 is disposed between the outside pipe 16 and the inside pipe 17 and the detection device 20 is disposed between the drive device 19 and the inside pipe 17, it is possible to detect load modification of the test piece 12 directly as pressure fluctuation to the load cell 33, so that the measurement precision improves.

Moreover, the drive device 19 and the detection means 20 are arranged in the series condition between the outside pipe 16 and the inside pipe 17, so that the measurement precision improves more.

Because the body of the equipment 11 is structured with the outside pipe 16, the inside pipe 17, the test piece attachment 18, the movable device 19 and the detection device 20, so that the handling is rather easy.

As for the body of the equipment 11, as putting-on and off to the lid 15 can be done freely, when the test of many test pieces 12 is implemented in order, it is expected that the test is done efficiently without the complex work.

Because the testing device 10 for tested material is small in the whole and is composed simply, it is possible to make manufacturing cost low.

Also, in view of the structure of the body of the equipment 11, since the lid 15 doesn't need special processing in addition to the fixation hole 22, the mechanism of the liquid vessel 13 can be simplified, too. That is, when the test is done in the condition which made the temperature of liquid 14 constant, by storing up the liquid 14 in a suitable container and soaking the bottom tip of the body of the equipment 11 therein, the execution of test becomes possible in low cost.

Incidentally, the state of this invention isn't limited to the above-mentioned embodiment and the improvement and the deformation of the invention in the range which is possible to achieve the mentioned purpose of this invention are contained in the present invention.

Figure 4:
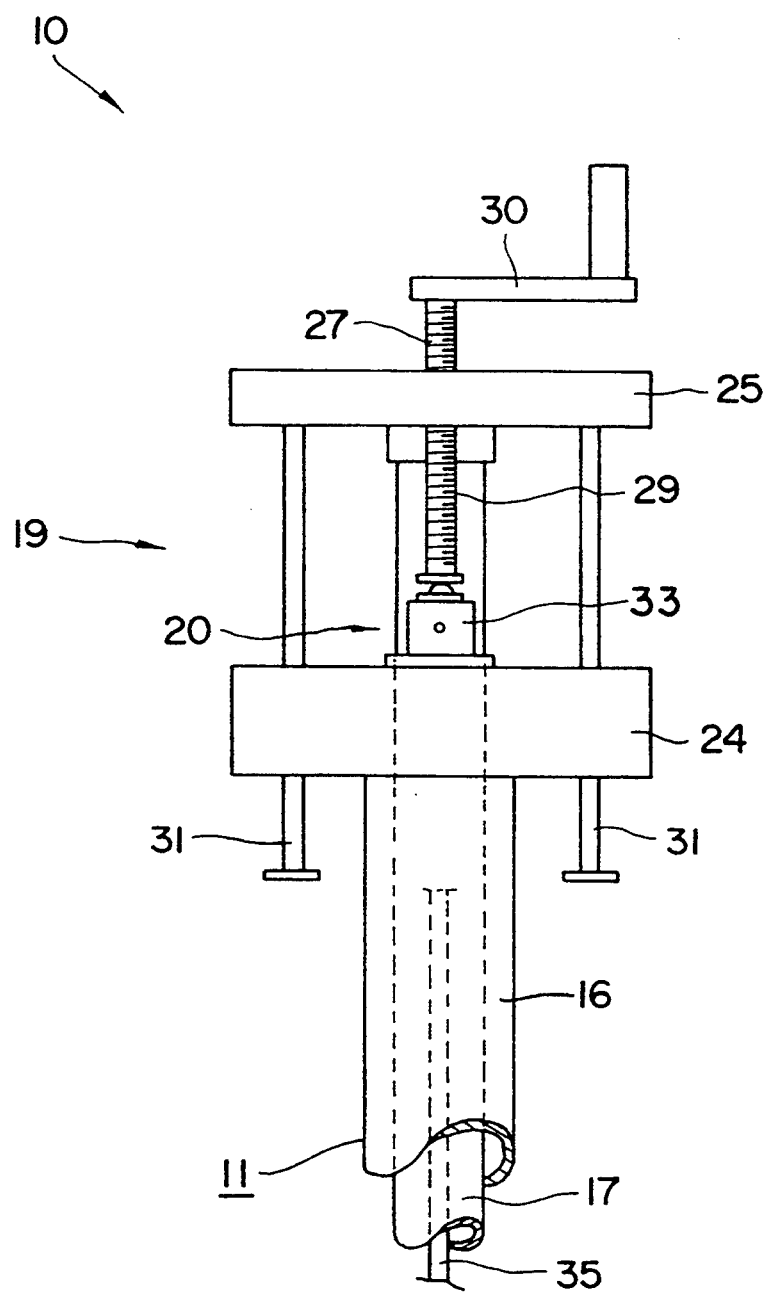
FIG. 4 is the sectional front view which shows the other embodiment according to the present invention.

FIG. 4 shows the other embodiment, wherein, referring to the detection device 20 of the body of equipment 11, the load cell 33 is put on the upper side of the support member 24 and the revolving shaft 27 of the drive device 19 is thrust into the pressure plate 25. From this structure, the above revolving shaft 27 presses the load cell 33 directly on its tip and the relative movement of outside pipe 16 and inside pipe 17 becomes possible as in the prior embodiment.

Accordingly, the number of parts composing the body of equipment 11 becomes more less. Moreover, since needed for processing tapered parts becomes unnecessary, the structure of the testing device 10 results in more simple one.

The first member and the second member may a member which is something other than a C-shaped member. It will not be a problem if such member has enough strength and the first member and the second member can move relatively.

In this embodiment, the outside pipe 16 and the inside pipe 17 were fixed in the condition which it stood in the almost vertical direction but it may be arranged in the horizontal direction. However, if the above-explained structure of the present invention is used, as the inside pipe 17 always moves down by the its own weight the device, to urge the inside pipe 17 in the lower direction is unnecessary and the mechanism of the body of equipment 11 is simple.

Though the mentioned equipment of the present invention was used to make the test piece 12 curve or bend repeatedly in the liquid 14, it is possible to use it in a test under atmospheric pressure and a test in which only curving is done.

Figure 5:
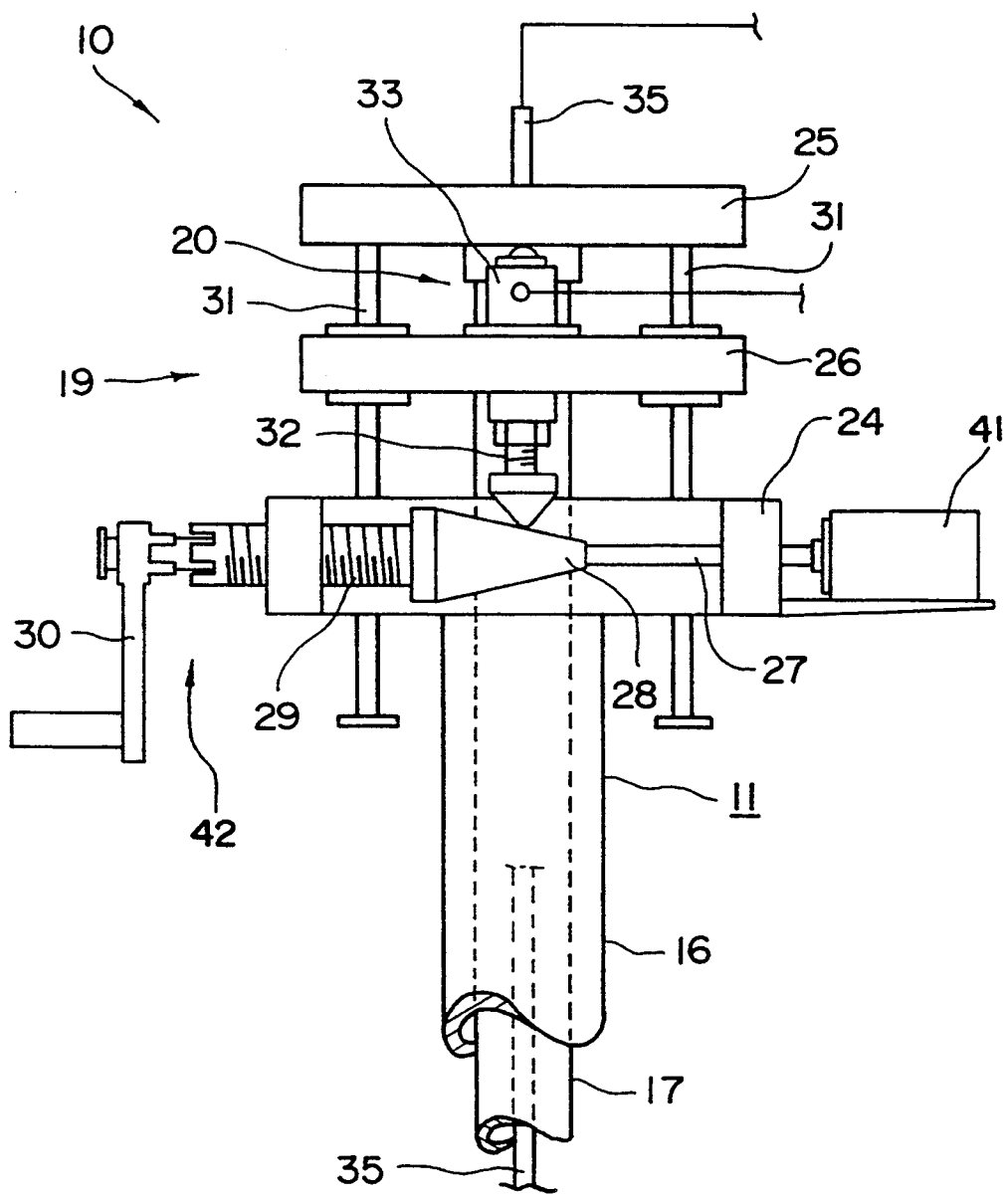
FIG. 5 is the view showing another modification of the rotation axle.

The rotation of revolving shaft 27 may be done by a method other than a manual one. One may attempt to automate a test with a suitable servomotor 41 as shown in FIG. 5. Incidentally, by connecting the servomotor 41 to a shaft end where the handle 31 of the revolving shaft 28 is not provided, and providing a handle through a claw 42 capable of engaging when the servo-motor is not operated, it is possible to achieve both a manual and an automatic operation mode at the same time. Also, one may adopt and then structure such as a rotatable cam and so on for the drive device in an embodiment, by which a repetition by constant displacement of the test piece becomes easy. As explained above, a making of the structural members in one body and arranging these members in series in this invention, makes the whole structure simple, achieves a compact construction with reduced weight and improves precision in the measurement of load, distortion and so on.

What is claimed is:

1. A material testing device, comprising:
  first and second relatively displaceable members;
  a test piece attachment device provided between common ends of said first and second members, the test piece bending in response to the relative displacement of said first and the second members;
  drive means oriented between said first and second members for displacing said first and second members relative to one another and from a position between ends of said first and the second members remote from said common ends;

said drive means being composed of a support member operatively connected to the remote end of said first member and includes a guide means thereon, a pressure plate operatively connected to the remote end of said second member and includes a pair of guide members guided by said guide means, and a sliding member arranged between said support member and said pressure plate and is guided by said guide members, said support member being in a form of a planar U with a rotation axle extending between two opposing sides of the U, the rotation axle being provided with a tapered portion arranged centrally between said opposing sides, a male screw portion being formed between the tapered portion and one end of the rotation axle, and a handle to turn the rotation axle so as to cause movement of the tapered portion back and forth; and detection means positioned at least one of between said drive means and said first member and between said drive means and said second member for detecting a load applied to the test piece.

2. A material testing device in claim 1, wherein said first and second members are, respectively, an outside cylinder and an inside cylinder arranged coaxially and spaced from one another.

3. A material testing device in claim 1, wherein said test piece attachment includes a pair of clips installed between each common end of said first and second members.

4. A material testing device in claim 1, wherein a servo-motor is provided and is connected to another end of said rotation axle, and wherein said handle is connected to one end of said rotation axle through a claw causing engagement of said handle to said rotation axle when said servo-motor is not operated, said rotation axle extending so that an axis thereof intersects the relative movement direction of the first and second members.

5. A material testing device in claim 1, wherein said detection means includes a load cell.

6. A material testing device in claim 1, wherein at least one of said first and second members is provided with a detachable means for facilitating a placement on and a removal from a vessel which contains said test piece.

* * * * *